(12) United States Patent
Iliffe-Moon et al.

(10) Patent No.: US 11,315,675 B2
(45) Date of Patent: Apr. 26, 2022

(54) SYSTEM AND METHOD FOR ENTRAINMENT OF A USER BASED ON BIO-RHYTHM OF THE USER

(71) Applicant: Bayerische Motoren Werke Aktiengesellschaft, Munich (DE)

(72) Inventors: Etienne Iliffe-Moon, Menlo Park, CA (US); Brian Mok, Santa Clara, CA (US); Dina Khaled Saber Amin Aladawy, Munich (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 0 days.

(21) Appl. No.: 16/792,965

(22) Filed: Feb. 18, 2020

(65) Prior Publication Data

US 2021/0257080 A1 Aug. 19, 2021

(51) Int. Cl.

| G08B 23/00 | (2006.01) |
|---|---|
| G16H 20/70 | (2018.01) |
| G06F 3/01 | (2006.01) |
| B60N 2/56 | (2006.01) |
| B60W 60/00 | (2020.01) |
| B60N 2/02 | (2006.01) |
| B60R 16/037 | (2006.01) |

(52) U.S. Cl.
CPC .............. *G16H 20/70* (2018.01); *G06F 3/015* (2013.01); *B60N 2/02* (2013.01); *B60N 2/56* (2013.01); *B60R 16/037* (2013.01); *B60W 60/0013* (2020.02); *B60W 60/0053* (2020.02); *G06F 2203/011* (2013.01)

(58) Field of Classification Search
CPC ... G16H 20/70; G06F 3/015; G06F 2203/011; B60W 60/0013; B60W 60/0053; B60N 2/02; B60N 2/56; B60R 16/037
USPC ........................................................ 340/576
See application file for complete search history.

(56) References Cited

U.S. PATENT DOCUMENTS

| 10,836,309 | B1 * | 11/2020 | Trundle | ............... G08G 1/0116 |
|---|---|---|---|---|
| 2014/0171752 | A1 * | 6/2014 | Park | .................... A61B 5/6893 |
| | | | | 600/301 |
| 2014/0218187 | A1 * | 8/2014 | Chun | ...................... A61B 5/18 |
| | | | | 340/439 |
| 2016/0167672 | A1 * | 6/2016 | Krueger | .............. A61B 5/7282 |
| | | | | 340/576 |
| 2017/0200449 | A1 * | 7/2017 | Penilla | .................. G10L 15/063 |
| 2018/0189681 | A1 * | 7/2018 | Harrivel | ................. G06F 3/011 |

(Continued)

*Primary Examiner* — Tai T Nguyen
(74) *Attorney, Agent, or Firm* — 2SPL Patent Attorneys PartG mbB; Kieran O'Leary

(57) ABSTRACT

A system and method for entrainment of a user based on bio rhythm of the user. The system includes an analyzing unit and an entraining rhythm generation unit. The analyzing unit receives bio rhythm information of a user, analyzes the bio rhythm information, and sets an entraining target based on an analysis of the bio rhythm information. The entraining rhythm generation unit generates an entraining rhythm based on the entraining target for providing an entrainment experience to the user, and control one or more human sensory inputs to the user based on the entraining rhythm. The bio-rhythm information may be information related to a breathing rate, a heart rate, brain waves, circadian rhythm, body rhythm, emotion, etc. The entrainment experience may be provided either inside or outside a vehicle.

20 Claims, 4 Drawing Sheets

(56) References Cited

U.S. PATENT DOCUMENTS

2019/0030278 A1* 1/2019 Kremer .............. A61B 5/4812
2019/0133511 A1* 5/2019 Migneco .............. B60N 2/002

* cited by examiner

SYSTEM AND METHOD FOR ENTRAINMENT OF A USER BASED ON BIO-RHYTHM OF THE USER

FIELD

Examples relate to a system and method for bio-entrainment of a user, more particularly, a system and method for an intelligent bio-rhythm entrainment that senses and monitors human bio-rhythms and creates an entrainment experience for a user that has a physiological and/or psychological effect to the user.

BACKGROUND

Technologies have been developed to provide more reliable driving and safety functions of a vehicle and provide a comfort to passengers in a vehicle. The vehicles may include autonomous electromechanical sensors for numerous driving, safety, and comfort functions. Systems such as in-car navigation devices and cruise control have been used, and systems such as smart cruise control, on-vehicle driver information systems, collision avoidance systems, vision enhancement, and roadworthiness diagnostics systems are also being developed.

SUMMARY

An example relates to a system for entrainment of a user based on bio rhythm of the user. The system may include an analyzing unit and an entraining rhythm generation unit. The analyzing unit may be configured to receive bio rhythm information of a user, analyze the bio rhythm information, and set an entraining target based on an analysis of the bio rhythm information. The bio-rhythm information may be information related to at least one of a breathing rate of the user, a heart rate of the user, brain waves of the user, circadian rhythm of the user, body rhythm of the user, or emotion of the user. The entraining rhythm generation unit may be configured to generate an entraining rhythm based on the entraining target for providing an entrainment experience to the user, and control one or more human sensory inputs to the user based on the entraining rhythm.

The system may further include at least one sensor or a sensing device configured to detect bio signals of the user and generate the bio rhythm information of the user. The sensor or sensing device may be integrated in a vehicle (e.g. in a seat, steering wheel, dashboard, etc.) depending on the type of the sensor or sensing device and whether the sensing requires physical contact or is contactless or remote sensing (e.g. camera or radar-based). The analyzing unit may be configured to receive the bio rhythm information from a user device. The user device may be one of a mobile phone, a tablet computer, or a wearable device worn by the user, etc.

The analyzing unit may be configured to set the entraining target based on a mode or multiple modes. The mode(s) may be set either automatically or manually by the user. The analyzing unit may be configured to set the mode based on an objective and a context of a user or vehicle. For example, in an automatic system, the entrainment experience may transition between modes seamlessly depending on the activities or features being used in the vehicle cabin. The mode may be one of a relaxation mode, an energizing mode, a sleep mode, an entertainment mode, a driving mode, or a safety mode, etc.

The entraining rhythm generation unit may be configured as a multi-sensory experience, such as to control at least one of lighting intensity and/or color, air flow, temperature, audio characteristics or audio content of an infotainment system, seat motion, position and massage features, and graphical features of user interface based on the entraining rhythm. The entrainment experience may be provided to the user with at least one of an on-board vehicle system, a smartphone, a table computer, a wearable device worn by the user, virtual reality (VR), augmented reality (AR), or mixed reality (MR). An on-board vehicle system is integrated or included within the vehicle, and may include graphical user interfaces such as a touch-screen, digital projection, VR/AR, etc. The entrainment experience may be provided either inside or outside a vehicle.

Another example relates to a method for entrainment of a user based on bio-rhythm(s) of the user. The method may include receiving bio rhythm information of a user, analyzing the bio rhythm information and setting an entraining target based on an analysis of the bio rhythm information, generating an entraining rhythm based on the entraining target for providing an entrainment experience to the user, and controlling one or more human sensory inputs to the user based on the entraining rhythm. The bio-rhythm information comprises information related to at least one of a breathing rate of the user, a heart rate of the user, brain waves of the user, circadian rhythm of the user, body rhythm of the user, or emotion of the user. The bio-rhythm information may be received from a user device.

At least one of lighting intensity and/or color, air flow, temperature, audio characteristics and music and/or media of an infotainment system, seat system, and graphical features of user interfaces may be controlled based on the entraining rhythm of the entrainment experience. The entrainment experience may be provided to the user with at least one of an on-board vehicle system, a smartphone, a table computer, a smartwatch, any wearable device worn by the user (e.g. a VR, AR, or MR head mounted display or smart glasses).

BRIEF DESCRIPTION OF THE FIGURES

Some examples of apparatuses and/or methods will be described in the following by way of example only, and with reference to the accompanying figures, in which.

DETAILED DESCRIPTION

Figure 1:
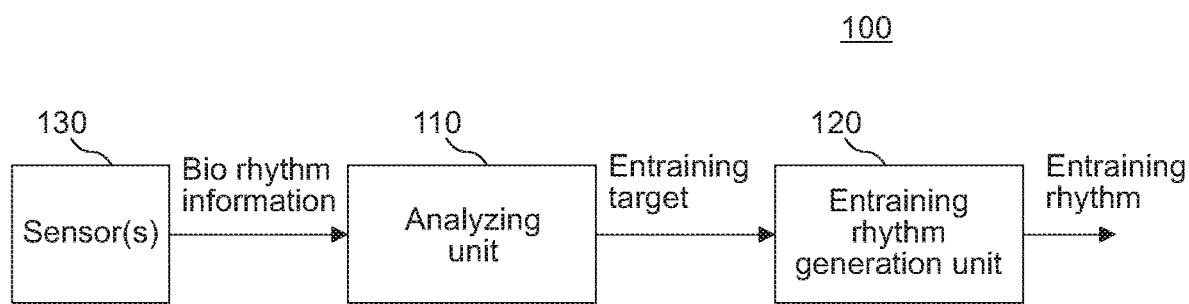
FIG. 1 is a schematic block diagram of an example system for an intelligent bio-rhythm entrainment in accordance with one example.

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B. An alternative wording for the same combinations is "at least one of A and B". The same applies for combinations of more than 2 elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Examples are disclosed for a system and method for an intelligent bio-rhythm entrainment that senses and monitors human bio-rhythms and creates an entrainment experience for a user or provides an entrainment experience to the user, which has a physiological and/or psychological and/or emotional effect to the user. Entrainment is provided to, or experienced by, a user when a human body adapts in some way to some rhythm from an external source (e.g. a breathing rate of a user gets lowered to a level that the person gets relaxed). The entrainment experience may be voluntary or involuntary. The effect and/or sensation from the entrainment experience may be conscious or sub-conscious, or real or perceived.

The entrainment experience may be provided within a vehicle cabin. Alternatively, the entrainment experience may be provided outside a vehicle or in any place (e.g. in a room, office, etc.). The entrainment experience may be provided by, or implemented with, a device(s) in a vehicle cabin, or a user device(s) such as a mobile phone, a tablet, a smart device, a wearable device, a device for virtual reality (VR), or the like.

Hereinafter, the term "user" will be used to refer to a driver of a vehicle, a (non-driver) passenger of a vehicle, or any person riding in a vehicle, or in general any person using the bio-rhythm entrainment system disclosed herein.

FIG. 1 is a schematic block diagram of an example system 100 for an intelligent bio-rhythm entrainment in accordance with one example. The system 100 provides entrainment of a user based on bio rhythm of the user. The system 100 may include an analyzing unit 110 and an entrainment rhythm generation unit 120. The system 100 may further include a sensor(s) 130 for sensing bio signals or bio rhythm of a user.

The analyzing unit 110 may be configured to receive bio rhythm information of a user. A rhythm is any repeating sequence or pattern. A bio-rhythm is any rhythm that occurs in a human body. For example, the bio-rhythm may be breathing-related rhythm of the user (e.g. a breathing rate), heart-related rhythm of the user (e.g. a heart rate), brain waves of the user, circadian rhythm of the user, body rhythm of the user (any repetitive movement, behavior, or motion of a body or body parts), emotion of the user, menstrual cycle, etc.

The system 100 may include at least one sensor 130 configured to detect bio signals of the user and generate the bio rhythm information of the user. Sensors 130 may be used to monitor the user's bio-rhythms. A camera or a microphone is considered as a type of sensor. Different types of sensors may be provided to sense different types of bio signals and rhythms. The analyzing unit 110 may receive the bio-rhythm information directly from the sensor(s) 130. Alternatively, the analyzing unit 110 may receive the bio rhythm information from a user device including a sensor. For example, the user device may be a mobile phone, a tablet computer, a smartwatch, or any wearable device worn by the user, etc.

The analyzing unit 110 may then analyze the bio rhythm information, and set an entraining target based on an analysis of the bio rhythm information. The entraining target is a target bio rhythm or user's state that the system 100 attempts to achieve for an entrainment period. A human bio rhythm may be entrained progressively over a time and the entraining target may be set for each entrainment period. For example, the entraining target may be a certain breathing rate (e.g. expressed as breaths per minute (bpm)) of the user to achieve a relaxation experience. The entraining target may be incrementally or decrementally adjusted (e.g. reduced or increased progressively or gradually) in response to the user successfully reaching each incremental/decremental entraining target.

The analyzing unit 110 may set the entraining target based on a mode or context of the user or vehicle (e.g. user profile and history, vehicle occupants, physical activity or movement, day/time, weather, music (e.g. genre, tempo, volume, etc.), media (e.g. movie, game, app, etc.) vehicle speed (e.g. relative to speed limit), traffic, climate control temperature, scent, etc.). A different mode may be set for a different objective. For example, the objective may be relaxation, energizing, rest (e.g. sleep), entertainment, safe driving, or the like. The mode may be set according to the objective. The entraining target may be set differently for a different mode (e.g. the target breathing rate may be set differently for different mode/objective). The mode may be set manually by the user. Alternatively, the mode may be set automatically by the system 100. In this case, the analyzing unit 110 may set the mode based on an objective and a context.

The entraining rhythm generation unit 120 may be configured to generate an entraining rhythm based on the entraining target for providing an entrainment experience to the user, and control one or more human sensory inputs to the user based on the entraining rhythm. The entraining rhythm controls the rhythm of all human multi-sensory inputs inside or outside a vehicle. The entraining rhythm can be a pattern or time-based framework for synchronizing any sensory modalities, events, or experiences presented to the user. The primary purpose of the entraining rhythm is used for providing bio-feedback to the user to progressively adapt the user's bio rhythm for entrainment experience in a looping process (i.e. the user's bio rhythm may be entrained in multiple steps with a bio feedback loop). A secondary or alternative purpose of the entraining rhythm might be to provide an aesthetic or emotionally rewarding experience, such as one that comes from a beautiful experience.

The entraining rhythm is used as a beat or timing to control one or more human sensory inputs to the user. For example, the entraining rhythm generation unit 120 may generate the entraining rhythm to control at least one of lighting intensity and/or color, air flow, temperature, audio characteristics and/or musical content and/or media of an infotainment system, seat system, graphical features of user interface, or the like. The entraining rhythm generation unit 120 may control the time-related behavior, transitions, synchronization and operations of the experience(s). The audio characteristics (e.g. volume, fade, balance, spatial properties, etc.) as well as the musical content of the audio (e.g. rhythm, beat, tempo, melody, etc.) may be controlled in accordance with the entraining rhythm. The music may be procedurally generated or manipulated by a computer such that the music is in time/phase to the entraining rhythm. Similarly the media content, such as a movie, game or interactive app could be affected by the entraining rhythm. The vehicle seat system features that can be controlled in accordance with the entraining rhythm include motion, position, orientation, fit/size, massage, temperature, ventilation, etc.

The entraining rhythm may be a master (i.e. primary) rhythm determined based on the bio rhythm information. Alternatively, the entraining rhythm may be a slave (i.e. secondary) rhythm determined based on the master rhythm (e.g. where the slave rhythm has a phase relationship (defined using a mathematics or physics wave definition) to the master relationship). Alternatively, the entraining rhythm may be an arbitrary rhythm (e.g. determined by a fixed timing, e.g. based on research test or anecdotal data). The master rhythm may be generated based on a single data input/source (i.e. a single sensor or device) or an aggregation of multiple data inputs/sources (i.e. multiple sensors or devices). Different slave rhythms may be generated for different human sensory modalities or different systems or devices that deliver the sensory input(s) or experience to the user.

The entrainment experience may be provided to the user inside or outside a vehicle. The entrainment experience may be provided to the user with a user device, such as a smartphone, a table computer, a smartwatch, a wearable device worn by the user, a device implementing virtual reality (VR), augmented reality (AR), or mixed reality (MR), or the like. VR is a simulated experience that can be similar to or completely different from the real world. AR is an interactive experience of a real-world environment where the objects that reside in the real world are enhanced by computer-generated perceptual information across multiple human sensory modalities, including visual, auditory, haptic, somatosensory, and olfactory. MR is merging of real and virtual worlds to produce new environments and visualizations.

As an example, a case of entrainment of a breathing rate will be explained. It should be noted that the examples disclosed herein are applicable to entrainment of any bio-rhythm other than a breathing rate entrainment. A breathing rate of a user may be monitored with a sensor/camera. The mode (objective) may be set to a relaxation mode, which aims to provide relaxation for the user. Scientific research has shown that a breathing rate in the range of 5, 6, or 7 breaths per minute (bpm) optimizes relaxation. This is the entrainment goal in this example, i.e. the target that can provide or increase relaxation.

A normal breathing rate of ordinary people is around 20 bpm. A breathing rate may increase with physical activity and stress. The stress may be work-related or life-related stress, or stress from driving, such as driving in a traffic jam, or the user may feel stress when being late for an important appointment, etc. In such situation, the current breathing rate of the user is monitored and the bio-rhythm entrainment system 100 generates an entraining rhythm to provide relaxation for the user. The entraining rhythm is generated based on an entraining target for each entraining period. The breathing rate of the user is progressively entrained until it reaches 5, 6, or 7 bpm. For example, the entraining target may be initially set at 18 or 16 bpm. When the user shows signs of reducing their breathing rate to a range close to the entraining target the entraining target may be incrementally reduced by 2 to 4 bpm. This process is repeated until the user reaches the final entrainment goal (e.g. 5, 6 or 7 bpm). The entraining rhythm is used as a beat or timing to control one or more human sensory inputs to the user. One or more human sensory inputs are controlled based on the entraining rhythm to provide bio-feedback to progressively decrease the breathing rate over a period of time (e.g. 2-3 minutes, 5 minutes, 10 minutes, or any periods of time) until the user's breathing rate reaches the goal (e.g. 5, 6, or 7 bpm).

Figure 2:
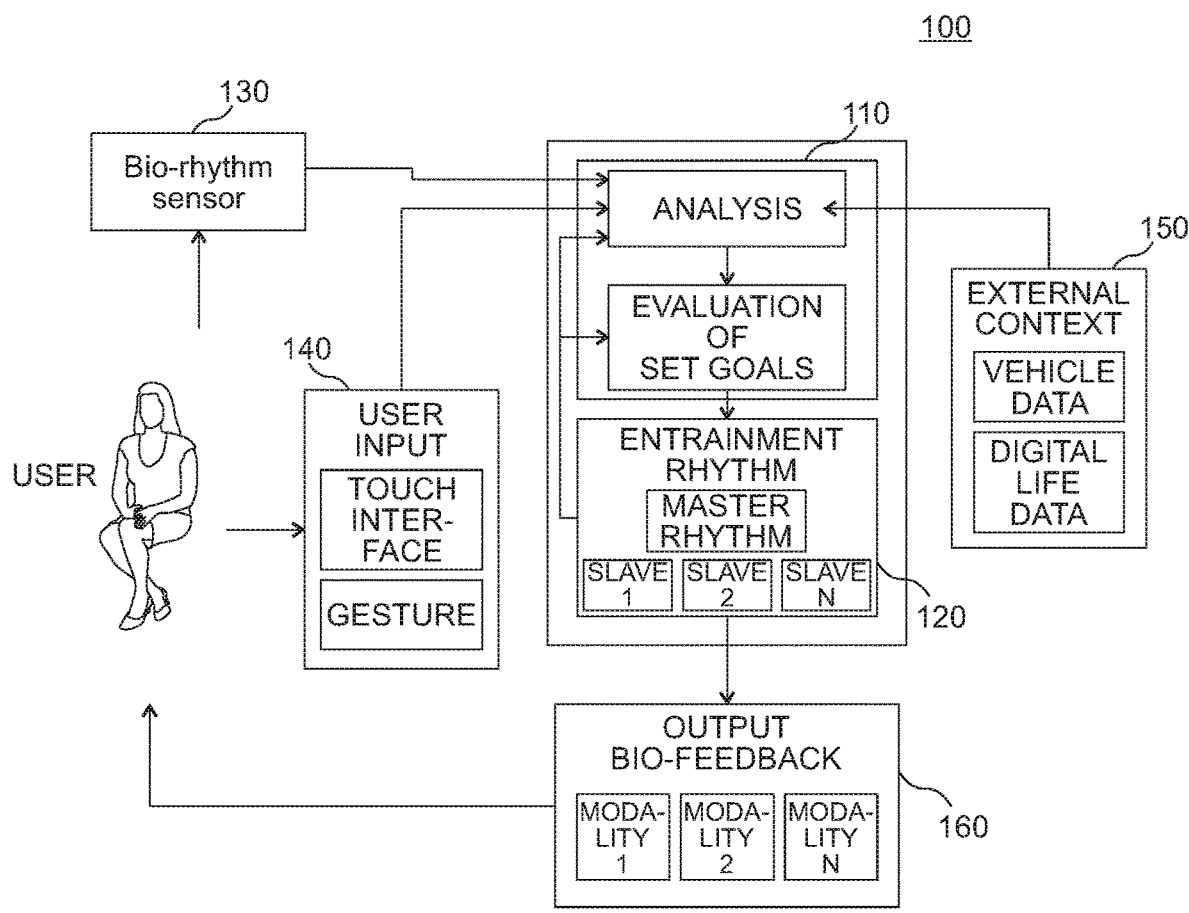
FIG. 2 shows the system for bio-rhythm entrainment in more detail.

FIG. 2 shows the system 100 for bio-rhythm entrainment in more detail. The system 100 includes an analyzing unit 110 and an entraining rhythm generation unit 120. The system 100 may further include a sensor 130 or sensors. The analyzing unit 110 receives bio rhythm information of a user and analyzes the received bio rhythm information.

Bio signals of a user may be sensed by a sensor(s) 130 and provided to the analyzing unit 110. A bio-rhythm is any rhythm (any repetitive sequence or pattern) that occurs in a human body. For example, the bio-rhythm may be a breathing rate of the user, a heart rate of the user, brain waves of the user, circadian rhythm of the user, body rhythm (any repetitive movement, behavior, or motion of a body or body parts) of the user, emotion of the user, etc.

A bio-rhythm may be sensed or monitored by measurement or prediction of physiological rates or signals of a user (i.e. bio-signals). Multiple sensors may be used to monitor user's bio-rhythms. In one example, physiological or biological rates (e.g. simple frequency information expressed as Hz, bpm, etc.) may be measured and reported as bio rhythm information. In another example, physiological signals or bio-signals may be measured and detailed rates and/or information may be extracted from the measured physiological signals or bio-signals. The measured signals may be complex signals that can provide information on cycle stages and phases of a human body. For example, heart beats or breathings may be sensed or measured by a sensor(s) and bio-rhythm information such as a heart rate (HR), heart rate variability (HRV) information, a respiration rate (RR), inhale-pause-exhale (IPE) timing, respiratory sinus arrhythmia (RSA), etc. may be extracted or reported to the analyzing unit 110.

The bio-rhythm may be determined by prediction, extrapolation, or interpolation of physiological rates or information. The prediction, extrapolation, or interpolation may be used if there are gaps in sensor data (e.g. due to limitations of the sensing technology, motion of the user, or interference from other signals) or where prediction, extrapolation, or interpolation may enhance the entrainment experience.

In some examples, a user state (i.e. a bio rhythm of a user, such as a breathing rate or heart rate) may be predicted or estimated by analyzing the historical data. The estimation or prediction of the user state may be made based on the last known or received data. For example, the running average calculated over a period of time may be used in estimating or predicting the user state. Alternatively, more complex mathematical interpolation may be used.

Alternatively, a user state (i.e. a bio rhythm of a user, such as a breathing rate or heart rate) may be predicted or estimated based on relationships with other bio-signal data from sensors. For example, a breathing rate of a user may be estimated from heart-related data (such as photoplethysmography (PPG) data, electrocardiography (ECG) data, or the like). The PPG or ECG data may be provided by on-board sensors on wearable devices such as smart watches and their apps.

In a hybrid approach, the historical data may be combined (factored) with any available other bio sensor data in estimating the state of the user.

In some example, the bio-rhythm may be self-reported information, rates or targets by a user. For example, the bio-rhythm may be reported by the user based on experience or aspirational goals of the user. The user may input a numerical value for a bio-rhythm (e.g. a breathing rate) or choose a mode or level (e.g. relaxation or meditation level) or type of experience, for example via a graphical user interface. Alternatively, a smart system may provide recommendation(s) or options for the user to choose and the user may choose one of the recommendations or options. Other examples of self-reported information includes sleep cycle (e.g. actual, estimated or aspirational) or menstrual cycle information.

The physiological/biological signals may be sensed and gathered directly by sensors or devices installed in a vehicle. The sensors and devices may be integrated with a vehicle. Alternatively or additionally, the physiological/biological signals may be sensed and gathered by an external device(s) including sensor(s). For example, the external device(s) may be a user device 140 e.g. mobile devices, such as smartphones, smartwatches, and software apps (on the devices or in the cloud), etc.

One example of bio-rhythm sensed by a sensor is a breathing rate (respiration rate). The breathing rate/respiration rate is the number of breaths a person takes per minute. The breathing rate may be a total respiration cycle (i.e. breaths per minute), a respiration cycle without pauses (or without significant pauses), a respiration cycle with pauses (inhale, pause (intra-pause), exhale, and pause between cycles (inter-pause)), or an RSA. Generally, sensors can provide average or instantaneous respiration rates. It is also possible to detect inhalation and exhalation phases of breathing (e.g. using a camera, a strain gauge (i.e. for sensing chest expansion/motion), microphone or radar sensing techniques).

Respiration control may be voluntary or involuntary. Respiration is a unique physiological process that is normally an unconscious, involuntary and autonomous physiological process. Yet the human can over-ride the autonomous control and control it entirely voluntarily, deciding when to breathe and how deeply. With the right entrainment conditions, it may be possible for respiration control to be less conscious and more subconscious. For example, in a similar way to how a couple of people walking together, may walk in synchronization without consciously being aware of or intentionally walking in step.

Other examples of bio-rhythms sensed by a sensor(s) include a heart rate or heart rate variability (HRV). Smartwatches or other wearable devices may use PPG or ECG sensors for monitoring a heart rate or HRV data. PPG is a technique for measuring the variation in the absorption of light by human skin. PPG has been used for heart rate measurement. ECG is a test that measures the electrical activity of the heartbeat. Remote photo-plethysmography (RPPG) is a camera-based method to estimate a heart rate and HRV. RPPG is used for measuring cardiac pulse rates from live or recorded video. A vehicle may include a driver-facing camera in a vehicle cabin and this driver-facing camera may be used to detect heart-related bio rhythm using the RPPG. In some examples, stress levels of a user may be estimated from the HRV data. An application(s) running on smartwatches, smartphones, or any user device may gather and share the data (e.g. directly or via a network (cloud)).

Other examples of bio-rhythms sensed by a sensor(s) include brain waves (e.g. brain signals such as alpha waves). Brain waves are oscillating electrical voltages in a human brain. Alpha waves are one type of brain waves. Sensing brain waves may require a head-mounted wearable device. Alternatively, sensors may be placed in the headrest of a vehicle seat.

Bio-rhythms sensed by a sensor(s) may include circadian rhythms (e.g. sleep or napping patterns). There are relationships between bio-rhythms (such as respiration and heart rates) and sleep patterns. Sleep, naps, and jetlag may be considered as rhythmic experiences that can be designed in the context of a vehicle cabin. In one example, breathing control and entrainment may create relaxation that also appears to induce sleepiness.

There is a research showing that naps should not be longer that around 15 minutes to avoid sleep inertia (a "grogginess" that is a physiological state of impaired cognitive and sensory-motor performance that comes after sleep, especially broken sleep). A breathing rate in non-rapid eye movement (REM) sleep becomes lower and more regular than during REM sleep and when awake. During REM sleep, eyes move quickly in different directions. It does not happen during non-REM sleep. A sleep pattern of a user may be self-reported or estimated from physical behaviors such as motion and eye closure and bio-signals such as heart rate.

A combination of bio data may be used to measure or sense a sleep state and phase of sleep of a user. For example, smartwatches or other wearable devices (including an app or algorithms in those devices) may estimate a sleep state and phase of sleep of a user by evaluating physical motion/activity and heart rate data of the user. Alternatively, an integrated camera provided in a vehicle cabin, in a room, or in other places may be used to sense or monitor eye closure of a user and estimate a heart rate (e.g. using RPPG) of a user and these data may be used to estimate or sense a sleep state or pattern of the user.

The user may activate a sleep mode or self-report the desire to sleep. A sleep mode may be set up to provide an entrainment experience to relax the user and induce sleep. This can be combined with a multi-sensory experience, for example, user interface, lighting, sound (music, white noise, etc.), temperature, air flow, etc. The user interface, lighting, sound (music, white noise, etc.), temperature, air flow, etc. may be controlled in accordance with an entraining rhythm to induce sleep and/or relaxation of the user. Studies have shown that body temperature plays a role in inducing sleep, for example heating the body (e.g. by climate control or seat heating) before sleep time and cooling the body after onset of sleep or during sleep improves the transition through sleep phases and quality of sleep. The user may preselect a sleep duration or alternatively the system may calculate a sleep time or recommended sleep time according to the journey duration (e.g. from the vehicle navigation system or smart device navigation device) and adjust the multi-sensory experience to gently wake up the user in the lightest sleep phase and avoiding the stage 3 sleep phase. Studies have shown that abrupt awakening during stage 3 sleep (slow-wave sleep (SWS)) produces more sleep inertia than awakening during sleep stages 1, 2 or REM sleep. The onset of slow-wave sleep occurs approximately 30 minutes after falling asleep, therefore a nap should be limited to under 30 minutes (or more optimally around 15 minutes) to prevent waking during slow-wave sleep and enhancing sleep inertia.

The sleep mode may include a nap mode as a sub-mode for a short nap (e.g. a 15-minute nap, or any period) rather than full deep sleep that might last for many hours. The nap mode would use multi-sensory bio-rhythm entrainment and a rhythm to the experience that correlates with an overall nap time (e.g. 15 minutes) with transitions into and out of the nap sleep. Multi-sensory inputs (user interface, lighting, sound, temperature, air flow, etc.) may be used and controlled in a certain rhythm to induce sleep and then wake up the user naturally (e.g. by increased loudness of audio, adjusting the light (e.g. by increased intensity and/or cooler blue-toned light, etc.), adjusting the climate control (e.g. by increased air flow and/or reduced temperature), diffusing a scent, etc.

Circadian rhythms are sleep patterns that also relate to the entrainment with daytime and nighttime periods. Sleep patterns are typically 90-minute cycles that include the main non-REM and REM sleep stages. It is possible to detect the REM sleep stages with a one-lead ECG or potentially estimate REM sleep stages with a camera combined with machine learning.

Jet lag is caused by a disjoint in circadian rhythms. A light therapy has been shown as a way of correcting circadian rhythms. In some examples, a jetlag mode may be set up to enhance the cabin lighting (e.g. light intensity and/or color (e.g. cooler (blue-toned) white)) to reinforce the daytime period of the circadian rhythm and reduce the cabin lighting (e.g. brightness and/or color tone (e.g. warmer (red-toned) white color)) to reinforce the nighttime period of the circadian rhythm.

Bio-rhythms sensed by a sensor(s) may include body rhythms. Body rhythms are repetitive and externalized movements, behaviors, or motions of a body or body parts, such as walking, swaying, dancing, finger or foot tapping, etc. These behaviors and body motions may be considered as an externalized indication of entrainment to an internal rhythm (e.g. spontaneous beat) or external rhythm (e.g. any entrainment experience, music). Research has shown that humans use spontaneous behavioral synchrony (e.g. dancing, tapping, etc.) when they intend to make affiliative and social relationships (as means to connect individuals with others).

In one example, cameras and microphones combined with machine learning may be used to detect rhythmic physical activity. It can also look for how rhythmic activity is coordinated with music. By monitoring or looking out for this activity, the level of immersion, engagement and/or affinity in an experience may be measured, especially if there is an obvious beat to the entraining rhythm (e.g. audio, music, lighting, or the like).

Bio-rhythm sensed by a sensor(s) may include blinking. Blinking may be measured with the use of a camera. Blinking is correlated with stress, fatigue, and drowsiness (reduction in blink rate and increased eye closure). Research has shown that blinking and eye closure can be used to disengage attention (e.g. to focus one's thoughts), and blinking correlates with medical conditions such as Parkinson's disease and Tourettes syndrome.

Bio-rhythm sensed by a sensor(s) may include emotion. Emotion may not be a time-based physiological rhythm, but emotions can have patterns, driven by context and may be indirectly related to time and routine. Emotion may be sensed or monitored by a camera and relevant algorithm by detecting facial expressions, gestures, etc. For example, the indications of emotions (e.g. a smile for happiness/joy or brow furrow for anger, etc.) may be sensed, for example with a camera. The time-based metrics (e.g. patterns, rates, averages, etc.) may be monitored for emotions and those metrics may be used to drive or influence the experience or aspects of the sensory experience.

Referring to FIG. 2, the analyzing unit 110 receives the bio rhythm information of a user and analyzes and evaluates the received bio rhythm information. For example, the analyzing unit 110 may gather data from all sensors and extract the bio-rhythm data (relative to time) that is meaningful (e.g. heart rate, HRV, respiration rate and/or phase, etc.). The analyzing unit 110 may correlate the different bio-rhythm data relative to time (e.g. over a time-based graph), reference historical data, evaluate the physiological and psychological state of the user, evaluate inputs regarding the mode and/or objective of the system (e.g. as a user input via a GUI touch-screen interface or automatically based on context data), and make decisions on the goal of system and entrainment experience, which is used in the next steps to determine the entraining rhythm and multi-sensory experience and it's components. The analyzing unit 110 may record data over time as history.

The analyzing unit 110 then sets an entraining target based on the analysis of the bio rhythm information. The entraining target is a target bio rhythm or user's state that the system 100 attempts to achieve in each entrainment period. For example, a breathing rate of the user may be entrained in multiple steps until the breathing rate of the user reaches a goal of 5, 6, or 7 bpm for relaxation. The 5, 6, or 7 bpm is the ultimate goal for the entrainment in this example. An entraining target may be set for each entrainment period for gradual and progressive entrainment experience. For example, the entraining target may be set 1, 2, or 3 bpm lower than the sensed breathing rate in each entrainment period based on context, mode, etc.

The analyzing unit 110 sets the entraining target based on a mode (or an objective). Some examples of the mode/objective are calming or relaxation, energizing, sleep (including nap or jetlag), entertainment, driving or autonomous driving modes (e.g. ease and boost), safety alert, etc. A mode for calming or relaxation is for providing mental calmness or physical relaxation. A mode for energizing may be selected if a user wants to be active. A mode for sleep may be activated for getting a deep sleep or a nap or for rapid recovery from jetlag. A mode for entertainment may provide amusement for the user. A mode for driving or autonomous driving may be selected for optimum driving. A mode for safety alert may provide a safety alert to the user when needed. The analyzing unit 110 may set an entraining target for each mode (i.e. for each entrainment experience modality).

The mode may be set automatically by the system 100 or manually by the user. For manual selection, the analyzing unit 110 may make a recommendation for the user, and the user may make a decision based on the recommendation. If the mode is selected manually by the user, the user may select a mode via any user interaction or intervention. For example, the selection may be made by voice command by saying, e.g. "I'd like to relax" to select a relaxation mode or "I'd like to sleep" to select a sleep mode. The selection may be made via a user interface (e.g. a touch screen, or the like) provided in a vehicle. Alternatively, the selection may be inferred by the users behavior, for example if the user intentionally closes their eyes (eye closure is detected by camera) and/or exhibits drowsiness (if they are a passenger or in an autonomous vehicle) and/or reclines their seat to lie back and/or adjusts the infotainment system, etc.

Alternatively, the analyzing unit 110 may look at context data 150 and make a decision to set a mode. For example, the analyzing unit 110 may consider context of the user or vehicle, for example, user profile and history, vehicle occupants, physical activity or movement, day/time, weather, music (e.g. genre, tempo, volume, etc.), vehicle speed (e.g. relative to speed limit), traffic, climate control temperature, scent, data coming from the vehicle or user's digital life, and location (e.g. based on Global Positioning System (GPS) data), navigation, etc.

The digital life data of the user may include biometric and bio signal data and application data such as calendar, messages, health, social media application information, etc. For example, the analyzing unit 110 may consider, in selecting or recommending the mode, information regarding the state of mind and needs of the user (e.g. whether the user is stressed, tired or sleepy, or whether the user is returning from the airport, or whether the user is on a long or short trip, or the like).

With this scheme, a multi-sensory experience may be provided to the user that dynamically shifts between different states or modes (e.g. from calm to energizing). The mode (i.e. the objectives of the experience) may vary over time. For example, a mode may be set to calm the user down, but not to the extent of falling asleep. Alternatively, a mode may be set to calm the user down to take a nap quickly (15 minutes) before the user arrive at the destination in 20 minutes.

The entraining rhythm generation unit 120 generates an entraining rhythm based on the entraining target for providing an entrainment experience to the user, and control one or more human sensory inputs to the user based on the entraining rhythm. Entrainment is provided or experienced when a human body adapts in some way to some rhythm from an external source. Entrainment may be a voluntary or involuntary, conscious or sub-conscious. The entrainment may happen internally to the human body and/or be exhibited externally, e.g. brain waves, breathing, toe tapping, etc. The sensation of entrainment can be "actual entrainment" (e.g. some extent of physiological synchronization) or a "perceived entrainment" (e.g. similar to a placebo effect). It is not important whether the user experiences theoretical entrainment, but feels a sensation and has a perceived benefit.

The entrainment experiences are presented to the user with single, multi-modal, or multi-sensory inputs, stimuli or experiences. The entrainment experience may be provided within a vehicle or outside of a vehicle (in another location, such as at home). The entrainment experience may be delivered by a device(s) or a system(s) in a vehicle cabin, such as a climate control system (e.g. an air conditioner, a heater, etc.), an infotainment system, seating features (e.g. a seat massage, a seat heater or cooler, etc.), lighting, user interfaces, interior surfaces such as shades, interior panels, windows, moon/sun-roofs, etc. For example, the vehicle seat system (e.g. with features including position, motion, articulation, massage, temperature, airflow, etc.) embedded in a vehicle seat may be controlled in accordance with the entraining rhythm for providing the entrainment experience. Alternatively, the entrainment experience may be delivered by external or third-party devices, including smartphones, smartwatches, smart-glasses, or any wearable devices, or through virtual reality (VR), augmented reality (AR) or mixed reality (MR). Entrainment experiences can be stronger when multiple senses are stimulated simultaneously.

The entrainment experiences in accordance with examples disclosed herein may provide functional, aesthetic and/or emotional benefits, for example, relaxation and stress relief, alertness and attention to safety, moments of beauty, sensory reinforcement of existing use cases or experiences, etc.

The entraining rhythm controls the rhythm of all human multi-sensory inputs inside or outside a vehicle. The entraining rhythm can be a pattern or time-based framework for synchronizing any sensory modalities, events, or experiences presented to the user. The entraining rhythm represents a target rhythm for entrainment of the user. The entraining rhythm may comprise a number of elements. For example, the entraining rhythm generation unit 120 may control at least one of lighting intensity and/or color, air flow, temperature, audio characteristics of an infotainment system, seat system features, and graphical features of user interface in a vehicle based on the entraining rhythm.

The entraining rhythm is used as a beat or timing to control one or more human sensory inputs to the user. For example, lighting pulses may be generated in intensity and/or color in synchronization with the entraining rhythm (e.g. 6 bpm). The air flow may be controlled to fluctuate from high to low, or low to high, in synchronization with the entraining rhythm. The temperature may be controlled to fluctuate in time (or in a scaled phase relationship) to the entraining rhythm. The infotainment audio volume may be adjusted (e.g. from medium to high, etc.) in accordance with the entraining rhythm. The seat massage features may be activated, deactivated, or changed in time to the entraining rhythm. The user interface in a vehicle may be adjusted such that a graphical or motion graphics of the user interface may pulse with the entraining rhythm, and provide feedback on the status of the entrainment experience and the difference between the entrainment target (e.g. a breathing rate target) and the entraining rhythm (e.g. a current breathing rate). The system can also recognize that the user has successfully entrained to the entraining target or final entraining target, by altering the multi-sensory feedback to acknowledge or "celebrate" the entrainment, which would have a gamification effect.

For advanced users, the system may give guidance on whether to use chest breathing (people typically breathe through chest breathing) or diaphragmatic (belly) breathing. Studies have shown that diaphragmatic breathing has greater benefits over chest breathing with controlled breathing exercises.

The entraining rhythm generated by the entraining rhythm generator may be a master rhythm (primary rhythm), a slave rhythm(s) (secondary rhythms), or a timed pulse.

A master rhythm is a nominal "pacemaker." The master rhythm may be determined by an input from bio-rhythm sensor data. The bio-rhythm sensor data may be from a single data input/source or an aggregation of multiple data inputs/sources. The master rhythm may be driven by the input/source according to some modifier or parameter. For example, the master rhythm may be determined by the bio-rhythm sensor data from multiple inputs/sources proportionally (e.g. 1:1 ratio), by scaling the bio-rhythm sensor data (e.g. by scaling the amplitude, proportion, phase, etc.), or by modifying the bio-rhythm sensor data (e.g. by a mathematical equation or algorithm). The master rhythm may be an output to an entrainment experience in itself. Alternatively, the master rhythm may drive a number of outputs of different modalities (i.e. slave rhythms). The master rhythm may be considered as a master clock that controls all other clocks (slave rhythms).

A slave rhythm is a secondary rhythm(s) that can be generated to adapt the master rhythm for different sensory modalities (modes), enhance entrainment, and foster the process or progress of entrainment. The slave rhythm may be driven by the master rhythm according to some modifier or parameter, for example proportionally (e.g. 1:1 ratio), scaled (e.g. by scaling the amplitude, proportion, phase, etc.) or modified (by a mathematical equation or algorithm). Different slave rhythms may be generated for different modes (different sensory modalities) or different systems or devices that deliver a sensory input(s) or experience to the user.

As an example, the slave rhythm can be considered as the number of beats in a musical bar. The number of beats can be scaled to adjust the nature of the experience, yet still maintain a phase relationship with the master rhythm (e.g. the bar or beats, depending on whether to scale the frequency up or down). An example of the slave rhythm could be a heart rate. The normal resting heart rate is typically 60-100 beats. How to represent a heart rate as a bio-feedback signal depends on the experience mode/objective (e.g. calming vs. energizing). For example, flashing an ambient light at 60 bpm may be energizing. The idea of a slave rhythm may be used to scale the rate of the ambient light to be more calming (or energizing) by using a different factor, e.g. a factor of 2 (for energizing=30 bpm) vs. 10 (for calming=6 bpm).

A timed pulse is a time-based rhythm based on a timed sequence or pattern. A timed pulse may be an arbitrary rhythm. A timed pulse may be used in cases where sensor data is not available for the entraining rhythm to be set relative to a bio-rhythm. A timed rhythm may be introduced to bring some variability or dynamics into the overall experience, or at specific times before or after the experience (e.g. as a welcome or goodbye when the user enters or exits the vehicle).

The entraining rhythm is used for providing an entrainment experience to the user. The entraining rhythm is intended to control a rhythm of one or more human sensory inputs. The entrainment experience is an interpretation of the entraining rhythm. The entrainment experience essentially provides bio-feedback 160 to the user. This bio feedback 160 allows the user to consciously or sub-consciously (voluntarily or involuntarily) adapt their behavior or activity (e.g. physiological or psychological) to the status communicated by the bio-feedback. The bio-feedback 160 is designed as a single or multi-sensory experience or multi-modal experience (modality 1 . . . modality N). The bio-feedback 160 functions as a feedback loop to adapt the entraining rhythm and the entrainment experience.

As the bio feedback is provided to the user, new bio-rhythm or user state is sensed by a sensor or a user device, and the system 100 compares the new bio-rhythm information against the entraining target and adapts the entraining rhythm and entrainment experience accordingly.

As an example for bio-rhythm entrainment, a case for breathing (respiration) rate control for providing relaxation is explained hereafter. The definitions of the symbols used in the equations or expressions are as follows.

$B_G$: Entrainment breathing rate goal (bpm), i.e. a final breathing rate target. Scientific research has shown that breathing at 5 to 7 bpm induces the optimal relaxation state. This also coincides with the Meyer Wave frequency of 0.1 Hz (0.1 cycles per second, which is 6 bpm). Studies have linked this to HRV and RSA.

$B_A$: Actual breathing rate (bpm) of a user.

$B_T$: Target breathing rate (bpm) that is progressively updated or changed according to the actual breathing rate ($B_A$). The target breathing rate is adjusted dynamically.

$L_G$: Length of one (1) breathing cycle (sec), i.e. the time length of a single breath (i.e. inhale and exhale), where $L_G=60/B_G$.

$\Delta B_G$: Difference in breathing rates (bpm) between the entrainment breathing rate goal and the actual breathing rate of the user, where $\Delta B_G=B_A-B_G$.

$\Delta B_T$: Difference in breathing rates (bpm) between the target breathing rate and the actual breathing rate of the user, where $\Delta B_T=B_A-B_T$, or $B_T=B_A-\Delta B_T$. For normal users, $\Delta B_T$ may be set to 1 bpm, such that the target breathing rate ($B_T$) will be reduced by 1 bpm per entrainment period (P). For advanced users, $\Delta B_T$ may be set to 2 or 3 bpm or dependent on the situation or scenario (e.g. context dependent).

F: Target breathing rate adjustment/reduction factor, i.e. a constant that can be set to adapt the system to differentiate users, situations, or scenarios (e.g. context dependent). For a normal user, F may be set to 0.5, whilst an experienced user may have a factor (F) that is higher or lower dependent on the circumstances. For example, a higher F requires more sustained breathing control, whilst a lower F requires more rapid changes in breathing.

P: Entrainment period (sec), i.e. a time period of entrainment to reach the breathing rate target ($B_T$), where $P=F \times L_G$.

The system 100 operates to reduce the breathing rate of the user by $\Delta B_T$ at the beginning of each entrainment period P. For example, for a normal user, $\Delta B_T=1$ bpm reduction every P seconds. At every time period P, the breathing rate of the user is progressively lowered until the breathing rate of the user reaches the entrainment breathing rate goal $B_G$ (i.e. $\Delta B_T=\Delta B_T=0$ when $B_A=B_G$). At this point, an entrainment occurs. When entrainment has occurred and the user is breathing at $B_G$ breathes per minute, the task for the user is to maintain the $B_G$ breathing rate for a certain period of time. Additional breathing exercises may then be conducted where the breathing rate is altered dynamically for exercise training and/or provide variations to maintain user engagement, interest and/or prevent fatigue. The system could also provide guidance on the type of breathing (e.g. chest or diaphragmatic breathing) the user should use.

As an example, it is assumed that a user is currently breathing at 21 bpm, and the goal of the entrainment experience is to reach relaxation at 6 bpm. For a normal user the breathing rate adjustment/reduction factor (F) may be set to 0.5. For a normal user the target breathing rate ($B_T$) may be reduced by 1 bpm ($\Delta B_T$) per entrainment period (P).

$B_A=21$ bpm, $B_G=6$ bpm, $L_G=60/B_G=10$ sec,

F=0.5, $\Delta B_T=1$, ($B_T$ is reduced by 1 bpm every period P ($B_T=B_A-\Delta B_T$), $\Delta B_G=21-6=15$ bpm, $P=F \times L_G=0.5 \times 10=5$ sec, i.e. the target breathing rate ($B_T$) is reduced every 5 seconds, $B_T=B_A-\Delta B_T=21-1=20$ bpm, i.e. the target breathing rate for the next period P is 20 bpm.

This loop is repeated once the user has achieved the target breathing rate, such that every period P of 5 seconds the target breathing rate is reduced until the user reaches the entrainment breathing rate goal ($B_G$) of 6 bpm for this example.

For example, at the second period P (e.g. from 5 to 10 seconds), $B_T$=19 bpm, at the third period P (e.g. from 10 to 15 seconds), $B_T$=18 bpm, at the fourth period P (e.g. from 15 to 20 seconds), $B_T$=17 bpm, and so on, until $B_T$=6 bpm=$B_G$.

The system 100 may adapt $\Delta B_T$ depending on the user, context, or system settings. For example, $\Delta B_T$ may be set to 2 or 3 bpm, which would increase the speed of entrainment and reduce the time it takes to reach $B_G$. For example, at the first time period (0-5 seconds), $B_T$=18 bpm, at the second time period (5-10 seconds), $B_T$=15 bpm, at the third time period (10-15 seconds), $B_T$=12 bpm, and so on, until $B_T$=$B_G$.

Figure 4A:
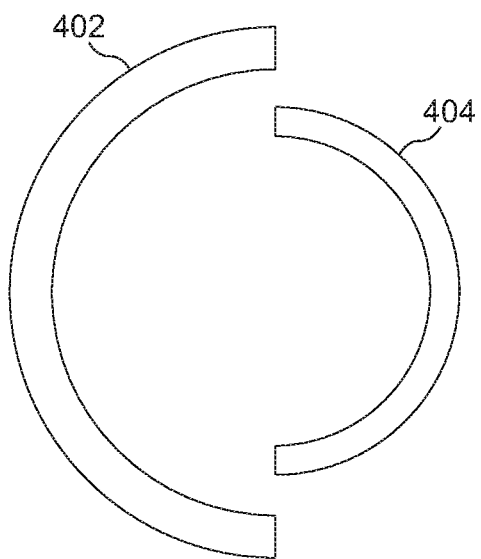
FIGS. 4A and 4B show an example interface displaying a current sensed breathing rate and a target breathing rate.
Figure 4B:
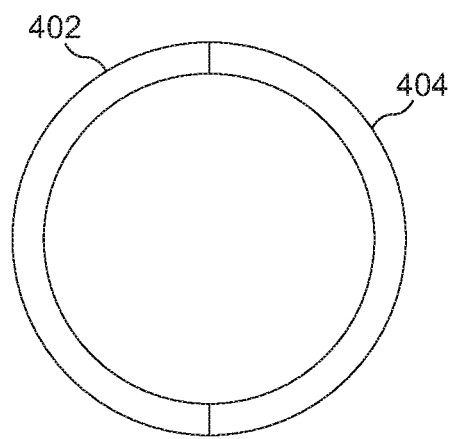

In this example, the sensory inputs to the user used for entrainment (bio-feedback) includes a GUI with semi-circular rings, as shown in FIGS. 4A and 4B as an example, (the GUI itself is a visual sensory input/stimulus to the user), ambient cabin lighting (e.g. (green) ambient cabin lighting that pulses with the (green) GUI semi-circle 402), audio characteristics (e.g. the audio volume and audio fade (front to rear spatial audio impression in the cabin) that pulses in phase to the (green) GUI semi-circle 402), seat system features (e.g. massage features and seat position move dynamically in phase to the (green) GUI semi-circle 402), the climate control (e.g. air flow would pulse with the (green) GUI semi-circle 402). These are multi-sensory examples of the sensory inputs the user would feel. The more sensory modalities the system engages in the user, the more immersive and intuitive the experience is. These inputs may be controlled by the system in coordination. The system may be centrally controlled (timing and commands are issued together (e.g. by a central electronic control unit). Alternatively, the system may be controlled in a distributed way (timing (by a central timing/control unit) and command instructions (e.g. by a local electronic control unit for each component in the system e.g. climate, seating, infotainment systems have separate ECUs) may be separate).

Once the user has successfully reached the $B_G$ goal rate, the system 100 can encourage the user to maintain entrainment over a period of time (e.g. 5 to 10 minutes, or any periods of time). After that period of time the system 100 can increase the breathing rate to a nominal rest rate as a transition to a more normal, natural and/or subconscious or autonomous breathing rate (e.g. 12 bpm). This increase may occur with the breathing rate adjustment factor F set at 0.5 or another value that may be higher or lower depending on the desired speed of level of breathing control the user should exert.

Alternatively, after the initial entrainment period (e.g. the first 5 to 10 minutes of entrainment) the system 100 may change the entrainment breathing rate goal $B_G$. For example, the entrainment breathing rate goal $B_G$ may be reduced to 5 bpm (following the same pattern) for a period of 3 minutes, then increased to 7 bpm for another period of time (e.g. 3 mins) and then return to 6 bpm or a different rate, before finally ending the experience. The experience may end as determined by the system settings, context, and/or by the choice of the user.

In some examples, the system 100 may include a user interface to provide feedback to the user. The user interface may have a graphic and motion graphics component. This user interface may provide bio-feedback of the actual breathing rate from sensor data and a visual comparison against a target breathing rate (e.g. a breathing rate of 6 bpm for relaxation). The user observes the user interface and attempts to achieve entrainment by matching the visual display of the actual breathing rate to the target breathing rate.

As shown in FIGS. 4A and 4B, the interface may display the current sensed breathing rate and the target breathing rate as two opposing semi-circular rings. It should be noted that the semi-circular shape of the interface in FIGS. 4A and 4B is merely an example and the visual interface may be in any shape or any color. The display may comprise two pulsating semi-circular rings 402, 404 (increasing and decreasing in size). One semi-circular ring 402 represents the entraining rhythm and the other semi-circular ring 404 represents the measured breathing rate. The semi-circular rings 402, 404 increase and decrease in size according to the current breathing rate (bpm). The goal is for the user to match the two semi-circular rings 402, 404 into a single completed circular ring with a unified behavior (e.g. in size, motion, timing, color, etc.) without mismatch, as shown in FIG. 4B. When this happens, the user reached entrainment at that rhythm frequency. This exercise may continue until the entrainment goal is reached (e.g. 6 bpm).

Examples are explained with reference to the breathing rate control, but the examples are applicable to different bio-rhythms and entrainment experiences and combinations thereof. For example, the entrainment system can be applied to a heart rate (e.g. in combination with a breathing rate) such that the actual heart rate shows signs of reduction in synchronization with a reduction in the target rate. This "gamification" of the entrainment process can create a new sensory experience that incentivizes entrainment, make it an objective and guided process and provide a high degree of satisfaction and reward.

Figure 3:
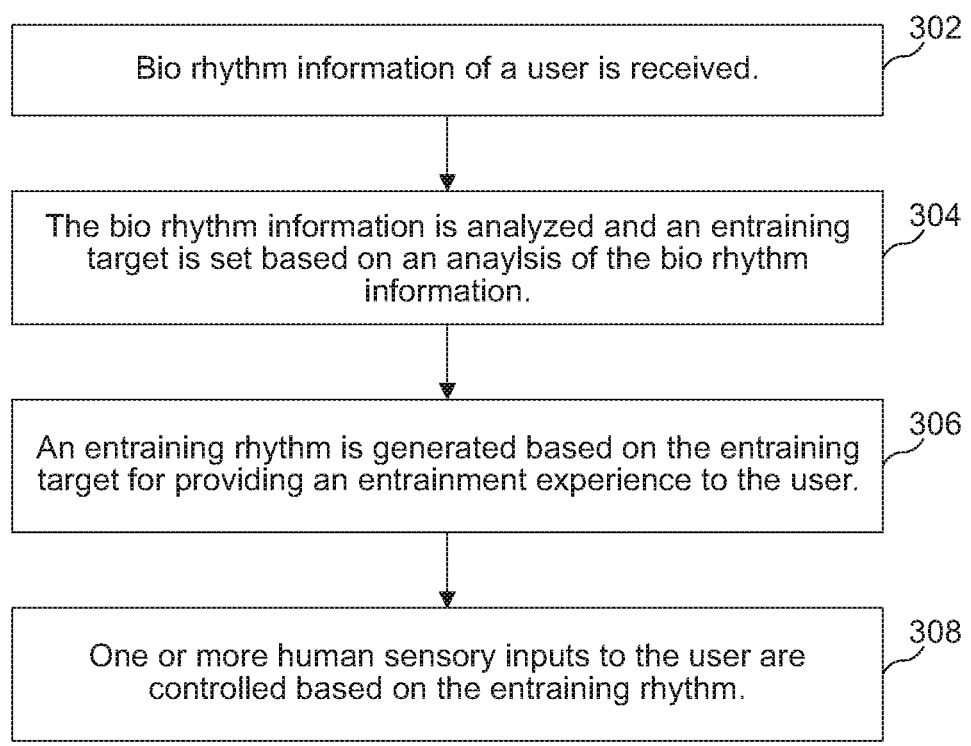
FIG. 3 is a flow diagram of an example process for entrainment of a user based on bio-rhythm of the user.

FIG. 3 is a flow diagram of an example process for entrainment of a user based on bio-rhythm of the user. The method includes receiving bio rhythm information of a user (302). The bio-rhythm information may be information related to at least one of a breathing rate of the user, a heart rate of the user, brain waves of the user, circadian rhythm of the user, body rhythm of the user, or emotion of the user. The bio rhythm information may be received directly from a sensor or sensors or from a user device including a sensor or sensors. The bio rhythm information is analyzed and an entraining target is set based on an analysis of the bio rhythm information (304). An entraining rhythm is generated based on the entraining target for providing an entrainment experience to the user (306). One or more human sensory inputs to the user are controlled based on the entraining rhythm (308). Entrainment may be provided by controlling at least one of lighting intensity and/or color, air flow, temperature, audio characteristics of an infotainment system, seat system features, and graphical features of user interface based on the entraining rhythm. The entrainment experience may be provided to the user with at least one of a smartphone, a table computer, a wearable device worn by the user, virtual reality (VR), augmented reality (AR), or mixed reality (MR). The entraining process of FIG. 3 may be implemented in a loop such that bio-feedback is provided to the user to progressively adapt the user's bio rhythm for entrainment experience in a looping process (i.e. the user's bio rhythm is entrained in multiple steps with a bio feedback loop).

Examples disclosed herein may be applied for an empathic vehicle. In such case, the goal is to create a real or perceived synergy between a vehicle and a passenger (a driver and a non-driver passenger), such as the perception that the vehicle understands the user or relates to the user.

The empathic vehicle can provide the impression that the brand and vehicle understand and relate to the user or passenger. The vehicle is tuned to the passenger(s) bio-rhythms.

The examples may also be applied for intelligent personal assistant (IPA) where the motion and timing of the IPA visualization has a rhythmic relationship to the entraining rhythm.

The examples may also be applied for user interfaces. The components of the user experience (e.g. motion graphics, illumination, sound, haptics, scent, etc.) may have a time-based or rhythmic relationship to the entraining rhythm. The entraining rhythm may be a master rhythm, a slave rhythm, or some timed rhythm. The entraining rhythm drives the behavior or expression of the graphics, illumination, sound, haptics, scent, etc. such that the experience is in-phase or has a phase relationship to the entraining rhythm. By analogy with musical/dance, the components of the user experience may be in step to the beat or in harmony to the entraining rhythm.

The examples may also be applied for mood lighting or spatial or surface illumination, for example, in an interior cabin or exterior illumination with a rhythmic relationship to the entraining rhythm.

The examples may also be applied for infotainment. It may influence the media, music, sound, noise-cancellation content or how it is played to the passengers of a vehicle. For example, the volume of the audio (loudness of music playing over the infotainment system) may be controlled in time to the entraining rhythm. This may work very well, especially in combination with other features like airflow and lighting. This feature may be applied/extended to any aspects of the infotainment system. The examples may be applied to the content of the music. For example, the music may be procedurally created or influenced in real-time, e.g. the beat or rhythm of the music may be altered. An example would be different "soundtracks" that are created to accompany different relaxation (calming) or energizing experiences.

In some examples, the acoustic properties or characteristics of the music may vary in time to the entraining rhythm. For example, volume (intensity or loudness) may vary from quiet to loud), fade (music direction) may move back and forth in the cabin, balance (music direction) may move from side to side in the cabin, noise cancellation (the clarity of the sound or outside street noise) may vary, tone or equalization (e.g. bass or treble intensity) may vary, etc.

This can also be combined with binaural audio to create an even stronger spatial affect with audio acoustics (e.g. the direction that the music seems to come from varies along-side the entraining rhythm).

The examples may also be applied for climate control and heating ventilation and air conditioning (i.e. heating, ventilation, and air conditioning (HVAC)) controlling the rhythmic relationship between air flow and other HVAC functions.

The examples may also be applied for body support or seating in a vehicle. The functionality, features and sensory modalities may have a rhythmic relationship to the entraining rhythm. For example, seat massage features, seat adjustment and motion, seat surface motion and/or haptics, surface temperature, air flow passing under or over the supported body, etc. may all be driven in a relationship to one or more bio-rhythms.

The examples may also be applied for manual and autonomous driving vehicle performance or behavior. For example, the speed of acceleration or deceleration (braking, if not safety critical) may vary according to some factor to the entraining rhythm or actual bio-rhythm (e.g. actual breathing rate or heart rate, etc.). This may vary in accordance with a direct or inverse relationship. For example, a high heart rate can come from stress or excitement. A small amount of stress and excitement may be a good thing (for fun and/or safety) but too much is a bad thing. By monitoring a heart rate and an HRV it can determine when to increase performance (with low to moderate stress or excitement) or reduce performance (and increase safety) of the autonomous vehicle driving systems or vehicle/driving performance (with high levels of stress). This may add an intelligent aspect to ease and boost functions of a vehicle.

The examples may also be applied for other vehicle features, such as interior and exterior lighting, sun shades, windows, interior and exterior surface panels, windscreen wipers, etc.

The examples may also be applied for the combination of all or multiple applications from the above examples into a holistic multi-modal or multi-sensory experience.

The examples may also be applied to multiple users. The system may provide the entrainment experience specifically to each user or some of the users simultaneously. The system may recognize a plurality of users (in a vehicle cabin), and the zone or seat each user is sitting in and deliver the entrainment experience specifically to each user or some of the users. For example, with a personal GUI interface and localized/zoned features (e.g. localized ambient lighting, localized climate control, and zoned audio, etc.), the entrainment experience may be delivered mostly or entirely to each specific user.

Another example is a computer program having a program code for performing at least one of the methods described herein, when the computer program is executed on a computer, a processor, or a programmable hardware component. Another example is a machine-readable storage including machine readable instructions, when executed, to implement a method or realize an apparatus as described herein. A further example is a machine-readable medium including code, when executed, to cause a machine to perform any of the methods described herein.

The aspects and features mentioned and described together with one or more of the previously detailed examples and figures, may as well be combined with one or more of the other examples in order to replace a like feature of the other example or in order to additionally introduce the feature to the other example.

Examples may further be or relate to a computer program having a program code for performing one or more of the above methods, when the computer program is executed on a computer or processor. Steps, operations or processes of various above-described methods may be performed by programmed computers or processors. Examples may also cover program storage devices such as digital data storage media, which are machine, processor or computer readable and encode machine-executable, processor-executable or computer-executable programs of instructions. The instructions perform or cause performing some or all of the acts of the above-described methods. The program storage devices may comprise or be, for instance, digital memories, magnetic storage media such as magnetic disks and magnetic tapes, hard drives, or optically readable digital data storage media. Further examples may also cover computers, processors or control units programmed to perform the acts of the above-described methods or (field) programmable logic arrays ((F)PLAs) or (field) programmable gate arrays ((F)PGAs), programmed to perform the acts of the above-described methods.

The description and drawings merely illustrate the principles of the disclosure. Furthermore, all examples recited herein are principally intended expressly to be only for pedagogical purposes to aid the reader in understanding the principles of the disclosure and the concepts contributed by the inventor(s) to furthering the art. All statements herein reciting principles, aspects, and examples of the disclosure, as well as specific examples thereof, are intended to encompass equivalents thereof.

A functional block denoted as "means for . . . " performing a certain function may refer to a circuit that is configured to perform a certain function. Hence, a "means for s.th." may be implemented as a "means configured to or suited for s.th.", such as a device or a circuit configured to or suited for the respective task.

Functions of various elements shown in the figures, including any functional blocks labeled as "means", "means for providing a sensor signal", "means for generating a transmit signal.", etc., may be implemented in the form of dedicated hardware, such as "a signal provider", "a signal processing unit", "a processor", "a controller", etc. as well as hardware capable of executing software in association with appropriate software. When provided by a processor, the functions may be provided by a single dedicated processor, by a single shared processor, or by a plurality of individual processors, some of which or all of which may be shared. However, the term "processor" or "controller" is by far not limited to hardware exclusively capable of executing software but may include digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included.

A block diagram may, for instance, illustrate a high-level circuit diagram implementing the principles of the disclosure. Similarly, a flow chart, a flow diagram, a state transition diagram, a pseudo code, and the like may represent various processes, operations or steps, which may, for instance, be substantially represented in computer readable medium and so executed by a computer or processor, whether or not such computer or processor is explicitly shown. Methods disclosed in the specification or in the claims may be implemented by a device having means for performing each of the respective acts of these methods.

It is to be understood that the disclosure of multiple acts, processes, operations, steps or functions disclosed in the specification or claims may not be construed as to be within the specific order, unless explicitly or implicitly stated otherwise, for instance for technical reasons. Therefore, the disclosure of multiple acts or functions will not limit these to a particular order unless such acts or functions are not interchangeable for technical reasons. Furthermore, in some examples a single act, function, process, operation or step may include or may be broken into multiple sub-acts, -functions, -processes, -operations or -steps, respectively. Such sub acts may be included and part of the disclosure of this single act unless explicitly excluded.

Furthermore, the following claims are hereby incorporated into the detailed description, where each claim may stand on its own as a separate example. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to include also features of a claim to any other independent claim even if this claim is not directly made dependent to the independent claim.

What is claimed is:

1. A system, comprising an at least one processor, for entrainment of a user based on bio rhythm of the user, comprising:
   an analyzing unit using the at least one processor, the analyzing unit configured to:
      receive bio rhythm information of the user,
      analyze the bio rhythm information, and
      set an entraining target based on an analysis of the bio rhythm information,
      monitor the bio rhythm information of the user,
   wherein the analyzing unit is configured to:
      set a mode based on an objective and a context of a user or a vehicle, and
      set the entraining target based on the mode, wherein the entraining target is set differently for a different mode; and
   an entraining rhythm generation unit using the at least one processor, the entraining rhythm generation unit configured to:
      generate an entraining rhythm for providing an entrainment experience to the user,
      wherein the entraining rhythm is based on the bio rhythm information received from the user, wherein the entraining rhythm is progressively modified based on the monitored bio rhythm information to reach the entraining target, and
      control one or more human sensory inputs to the user based on the entraining rhythm.

2. The system of claim 1 wherein the bio-rhythm information is a breathing rate of the user.

3. The system of claim 1 wherein the bio-rhythm information comprises information related to at least one of a heart rate of the user, brain waves of the user, circadian rhythm of the user, body rhythm of the user, menstrual cycle, or emotion of the user.

4. The system of claim 1 further comprising:
   at least one sensor configured to detect bio signals of the user and generate the bio rhythm information of the user.

5. The system of claim 1, wherein the analyzing unit is configured to receive the bio rhythm information from a user device.

6. The system of claim 5, wherein the user device is one of a mobile phone, a tablet computer, or a wearable device worn by the user.

7. The system of claim 1, wherein the mode is set either automatically or manually by the user.

8. The system of claim 1, wherein the mode is one of a relaxation mode, an energizing mode, a sleep mode, an entertainment mode, a driving mode, or a safety mode.

9. The system of claim 1, wherein the entraining rhythm generation unit is configured to control at least one of lighting intensity and/or color, air flow, temperature, audio characteristics and/or music and/or media of an infotainment system, seat system features, and graphical features of user interface based on the entraining rhythm.

10. The system of claim 1, wherein the entrainment experience is provided to the user with at least one of a smartphone, a table computer, a smartwatch, a wearable device worn by the user, virtual reality (VR), augmented reality (AR), or mixed reality (MR).

11. The system of claim 1, wherein the entraining rhythm is a master rhythm and the entraining rhythm further comprises a slave rhythm determined based on the master rhythm, or an arbitrary rhythm.

12. The system of claim 1, wherein system is configured to recognize a plurality of users and a zone that each user is sitting in and provide the entrainment experience specifically to each or some of the users.

13. The system of claim 1 wherein the analyzing unit sets the entraining target for each of a plurality of entrainment periods, and wherein the entraining rhythm generation unit generates the entraining rhythm to reach the entraining target of each of the plurality of entrainment periods.

14. A method for entrainment of a user based on bio rhythm of a user, comprising:
    receiving bio rhythm information of the user;
    setting a mode based on an objective and a context of a user or a vehicle;
    analyzing the bio rhythm information and setting an entraining target based on an analysis of the bio rhythm information and the mode, wherein the entraining target is set differently for a different mode;
    monitoring the bio rhythm information of the user,
    generating an entraining rhythm for providing an entrainment experience to the user,
    wherein the entraining rhythm is based on the bio rhythm information received from the user, wherein the entraining rhythm is progressively modified based on the monitored bio rhythm information to reach the entraining target; and
    controlling one or more human sensory inputs to the user based on the entraining rhythm.

15. The method of claim 14 wherein the bio-rhythm information comprises information related to at least one of a breathing rate of the user, a heart rate of the user, brain waves of the user, circadian rhythm of the user, body rhythm of the user, menstrual cycle, or emotion of the user.

16. The method of claim 14, wherein the bio rhythm information is received from a user device.

17. The method of claim 14, wherein at least one of lighting intensity and/or color, air flow, temperature, audio characteristics and/or music and/or media of an infotainment system, seat system features, and graphical features of user interface is controlled based on the entraining rhythm.

18. The method of claim 14, wherein the entrainment experience is provided to the user with at least one of a smartphone, a table computer, a smartwatch, a wearable device worn by the user, virtual reality (VR), augmented reality (AR), or mixed reality (MR).

19. A non-transitory machine-readable storage including machine readable instructions, when executed, to implement a method of claim 14.

20. The method of claim 14 wherein the entrainment target is set for each of a plurality of entrainment periods and wherein the entraining rhythm is generated to reach the entraining target of each of the plurality of entrainment periods.

* * * * *